US012690899B2

(12) United States Patent
Hodrinsky et al.

(10) Patent No.: US 12,690,899 B2
(45) Date of Patent: Jul. 28, 2026

(54) SPINAL IMPLANT GRIPPING DEVICE WITH AUDIBLE LOCKING MECHANISM AND REVERSIBLE CLAMP FOR SECURE SURGICAL INSERTION

(71) Applicant: Nivalon Medical Technologies Inc., Mansfield Center, CT (US)

(72) Inventors: Todd W Hodrinsky, Mansfield Center, CT (US); Marcel Janse, Mansfield Center, CT (US)

( * ) Notice: Subject to any disclaimer, the term of this patent is extended or adjusted under 35 U.S.C. 154(b) by 0 days.

(21) Appl. No.: 19/004,296

(22) Filed: Dec. 28, 2024

(65) Prior Publication Data

US 2026/0183023 A1    Jul. 2, 2026

(51) Int. Cl.
  *A61F 2/46*      (2006.01)
  *A61B 17/70*     (2006.01)
  *A61B 17/00*     (2006.01)

(52) U.S. Cl.
  CPC . *A61B 17/7074* (2013.01); *A61B 2017/00115* (2013.01); *A61B 2017/00367* (2013.01)

(58) Field of Classification Search
  CPC ... A61F 2/4611; A61F 2/7074; A61B 17/7074
  See application file for complete search history.

(56) References Cited

U.S. PATENT DOCUMENTS

| | | | | |
|---|---|---|---|---|
| 3,136,040 A * | 6/1964 | Bauer | ............... | H01R 43/26 |
| | | | | 81/463 |
| 5,716,415 A * | 2/1998 | Steffee | ............... | A61F 2/447 |
| | | | | 623/17.16 |
| 6,319,257 B1 * | 11/2001 | Carignan | ............ | A61F 2/4601 |
| | | | | 606/205 |
| 2008/0119935 A1 * | 5/2008 | Alvarez | ............ | A61F 2/4611 |
| | | | | 606/151 |
| 2012/0197317 A1 * | 8/2012 | Lezama | ............ | A61F 2/4611 |
| | | | | 606/86 A |
| 2013/0204370 A1 * | 8/2013 | Danacioglu | ............ | A61F 2/447 |
| | | | | 623/17.16 |
| 2015/0190242 A1 * | 7/2015 | Blain | ............... | A61F 2/4611 |
| | | | | 623/17.12 |
| 2020/0030118 A1 * | 1/2020 | Italiaie | ............. | A61F 2/4611 |

* cited by examiner

*Primary Examiner* — Jan Christopher L Merene
(74) *Attorney, Agent, or Firm* — Sam Pierce

(57) ABSTRACT

A spinal implant gripping device comprising: a. a clip with living hinges configured to grip a spinal implant; b. a central threaded rod fixedly attached to the clip; c. a pusher that slides freely over the central threaded rod to actuate the clip's living hinges, causing the clip to securely grip the spinal implant; and d. an interchangeable nut and cap operable to extend or retract the gripping mechanism by rotating along the central threaded rod.

13 Claims, 4 Drawing Sheets

SPINAL IMPLANT GRIPPING DEVICE WITH AUDIBLE LOCKING MECHANISM AND REVERSIBLE CLAMP FOR SECURE SURGICAL INSERTION

BACKGROUND OF THE INVENTION

Field of Invention

The present invention relates to surgical tools, specifically a device designed for gripping and manipulating spinal implants during surgical procedures. The invention focuses on providing a secure and efficient means of handling spinal implants, incorporating a reversible clamping mechanism with living hinges, an audible locking feature, and a self-supporting design. These features enhance precision and reliability during insertion and removal, minimizing the risk of damage to delicate implant materials and improving surgical outcomes.

Brief Summary of the Invention

The present invention provides a spinal implant gripping device designed to securely hold and manipulate spinal implants during surgical procedures. The device comprises a clip with living hinges actuated by a central threaded rod, which expands the clip's wings to clamp the implant securely. An audible clicking mechanism signals full engagement, providing the surgeon with a clear indication that the implant is securely locked in place.

The device features a reversible design, allowing the central threaded rod to be rotated in the opposite direction to release the gripping mechanism and facilitate removal during the procedure. Additionally, the clip is constructed from durable yet non-damaging materials, such as plastic or metal, ensuring compatibility with fragile implant materials like ceramics.

The self-supporting nature of the locked device allows the surgeon to tap the implant into place using secondary tools, such as a hammer, without compromising the structural integrity of the implant. This invention enhances surgical precision, minimizes the risk of implant damage, and ensures ease of use for healthcare professionals.

DETAILED DESCRIPTION

Figure 1:
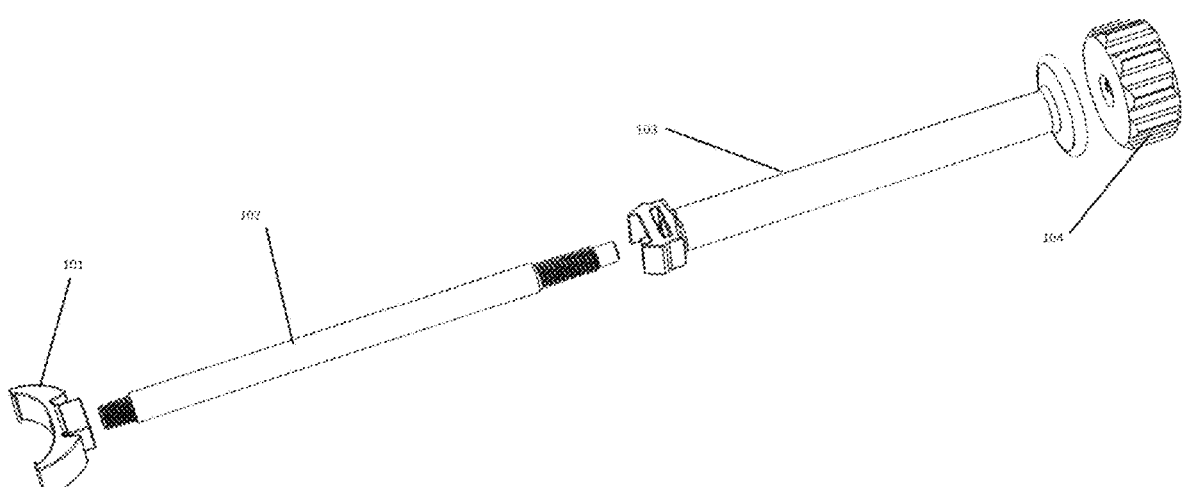
FIG. 1 illustrates all components of the spinal implant gripping device prior to assembly, including the clip (1.101), pusher (1.102), central threaded rod (1.103), and the interchangeable nut (1.104), with only this component capable of being connected at a time.

The present invention pertains to a novel spinal implant gripping device specifically designed to address the challenges associated with securely handling and manipulating spinal implants during surgical procedures. This device provides surgeons with a reliable and efficient means to grip and insert implants while minimizing the risk of damage to the implant itself, particularly when dealing with fragile materials like ceramics. Through its innovative combination of mechanical precision, safety features, and user-friendly design, the invention enhances the overall quality and outcomes of spinal surgeries.

At the heart of the invention is the clip (designated as 1.101), which serves as the primary gripping component. The clip is equipped with living hinges that enable its wings to open or close, forming a clamping mechanism that securely holds the spinal implant. These living hinges are designed to provide both flexibility and strength, ensuring the clip can grip the implant without causing deformation or fracture. Constructed from durable materials such as plastic or metal, the clip is engineered to withstand the rigors of surgical use while maintaining a gentle, non-damaging interface with the implant. Additionally, the contact surfaces of the clip are made from materials specifically chosen to prevent wear or damage to fragile implants, offering compatibility with a wide range of implant materials, including ceramics.

A key structural component of the device is the central threaded rod (designated as 1.103), which remains fixed and serves as the backbone of the device's mechanism. Threaded directly into the clip, this rod does not move during operation but instead acts as the anchor for the dynamic elements of the device. The top of the central threaded rod is outfitted with an interface for precise rotational control by the surgeon, allowing seamless integration with standard surgical tools and making the device intuitive and efficient to use.

Sliding along the central threaded rod is the pusher (designated as 1.102), a critical element responsible for actuating the clip's wings. The pusher is designed to move freely over the central threaded rod, enabling smooth and controlled operation of the clamping mechanism. By advancing the pusher along the rod, the surgeon can incrementally apply force to the living hinges of the clip, causing the wings to close and securely grip the implant. This progressive application of force prevents sudden pressure spikes that could damage the implant, ensuring a safe and reliable clamping process.

To facilitate the extension and retraction of the gripping mechanism, the device includes the interchangeable component: the insertion nut (designated as 1.104). This component can be used to adjust the position of the pusher, enabling the surgeon to either tighten the grip or release the implant as needed. This reversible design allows the device to adapt to various surgical scenarios, providing flexibility and control throughout the procedure.

One of the most distinctive features of the invention is its audible locking mechanism, which emits a clicking sound when the clip is fully engaged. This auditory feedback serves as a critical confirmation for the surgeon, ensuring that the device is securely locked in place. This feature not only enhances the surgeon's confidence but also reduces the likelihood of errors during the procedure. Furthermore, the device is equipped with safety mechanisms to prevent unintentional disengagement, ensuring that the implant remains securely held until removal is explicitly intended.

The invention's self-supporting design further adds to its utility. Once locked in place, the device can support itself on the implant, allowing the surgeon to use secondary tools, such as a hammer, to tap the implant into its final position. This design feature distributes forces evenly across the implant, minimizing the risk of damage while ensuring precise placement. By eliminating the need for the surgeon to manually stabilize the device, the self-supporting design also improves the ergonomics of the procedure.

Further to its mechanical functionality, the invention reflects careful consideration of material selection and safety. The clip's contact surfaces are made from non-damaging materials to protect the implant, while the living hinges are designed to provide consistent, controlled clamping forces. These design choices ensure that the device performs reliably across a variety of surgical scenarios, offering surgeons a robust and versatile tool for implant handling.

This spinal implant gripping device represents a significant advancement in surgical technology, combining innovative mechanical features, safety enhancements, and user-centric design to improve the handling and placement of spinal implants. Its precise operation, audible feedback, and adaptable design address the core challenges faced in spinal surgeries, ensuring that implants can be inserted and secured with maximum safety and efficiency. This invention not only improves the surgeon's ability to perform delicate procedures but also contributes to better outcomes for patients by safeguarding the integrity of the implant throughout the surgical process.

Detailed Description of Figures

FIG. 1 provides an overview of the individual components of the spinal implant gripping device in their pre-assembled state. The clip (1.101) is shown as the primary component designed to grip the spinal implant via its living hinges. The pusher (1.102), which slides over the central threaded rod (1.103), is displayed separately to highlight its structural independence. The central threaded rod (1.103) is depicted with threading to demonstrate how it interacts with the clip and the interchangeable components. The insertion nut (1.104) is shown, emphasizing that this component can be attached to the device to facilitate the gripping mechanism's operation.

Figure 2:
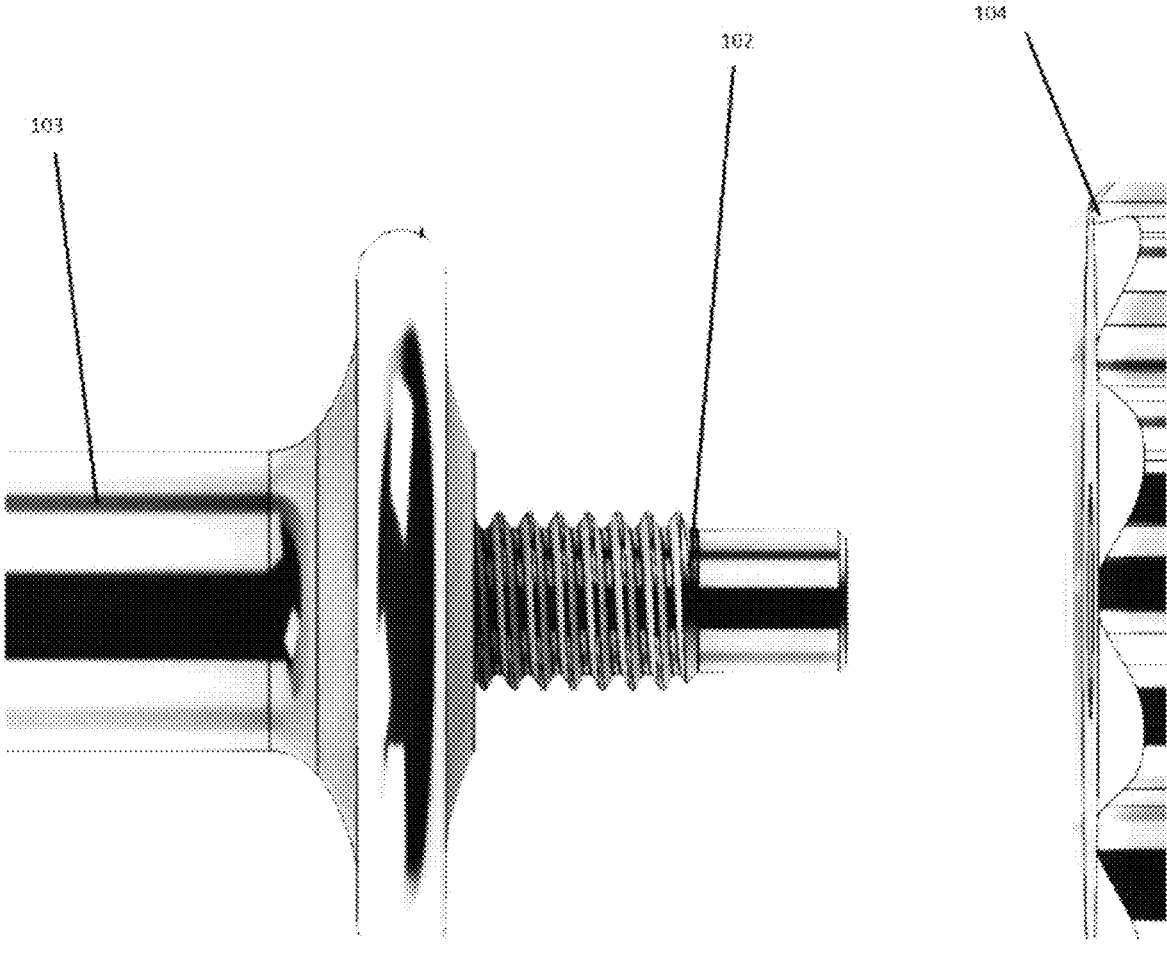
FIG. 2 provides a detailed view of the interaction between the central threaded rod (2.103) and the pusher (2.102), demonstrating their fit, with the insertion nut (2.104) included in this configuration.

FIG. 2 offers a close-up of the internal interaction between the central threaded rod (2.103) and the pusher (2.102), highlighting the alignment and structural design that allows the pusher to slide freely over the rod. The insertion nut (2.104) is included in this configuration, illustrating how it connects to the pusher and threaded rod to adjust the gripping force. This figure emphasizes the precision of the fit between the threaded rod and the pusher, demonstrating how these components contribute to the overall functionality of the gripping mechanism.

Figure 3:
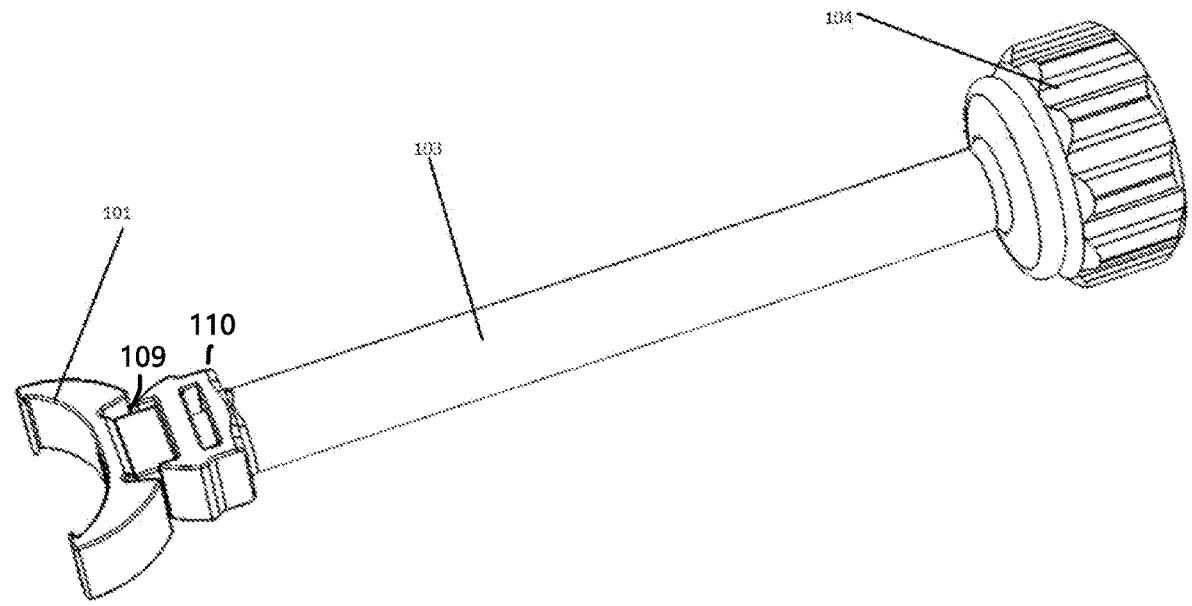
FIG. 3 details the internal connections between the clip (3.101), the pusher (3.102), the central threaded rod (3.103), and the insertion nut (3.104)

FIG. 3 focuses on the internal assembly of the spinal implant gripping device, specifically showcasing the interaction of the clip (3.101), the pusher, the central threaded rod (3.103), and the insertion nut (3.104). The figure demonstrates how the threaded rod is fixedly attached to the clip and how the pusher slides along it to actuate the clip's living hinges. The insertion nut (3.104) is shown threaded onto the rod, enabling the mechanism's operation for extending the clip's wings. The exclusion of the extraction cap highlights the specific configuration required for inserting and securing the implant.

Figure 4:
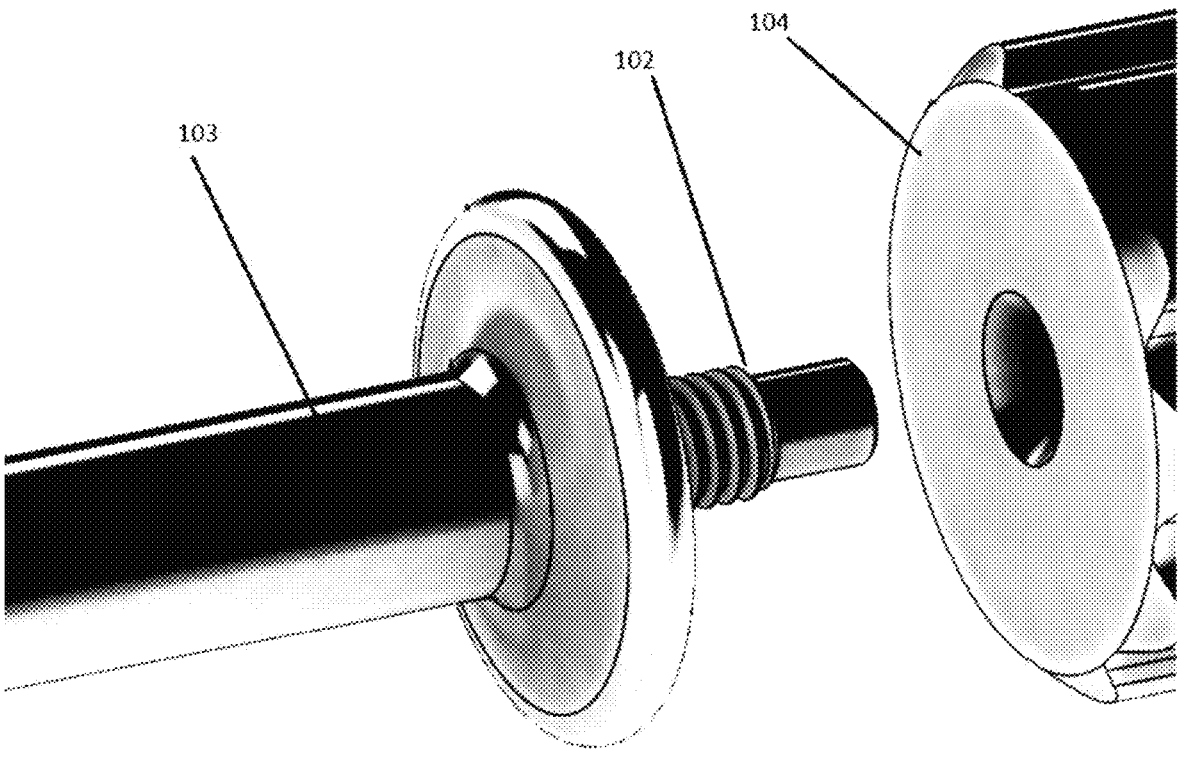
FIG. 4 illustrates the internal connections between the clip (4.101), the pusher (4.102), and the central threaded rod (4.103), with the insertion nut (4.104).

FIG. 4 depicts the internal configuration of the spinal implant gripping device with the clip (4.104), the pusher (4.102), and the central threaded rod (4.103). This configuration showcases how the insertion nut is used to adjust the pusher's position, tightening or loosening the clip's grip on the spinal implant. The detailed view highlights how the insertion nut interacts directly with both the pusher and the threaded rod, ensuring precise control over the gripping mechanism while maintaining structural integrity.

What is claimed is:

1. A spinal implant gripping device comprising: a. a clip with living hinges configured to grip a spinal implant; b. a central threaded rod fixedly attached to the clip; c. a pusher that slides freely over the central threaded rod to actuate the clip's living hinges, causing the clip to securely grip the spinal implant; and d. an interchangeable nut operable to extend or retract the gripping mechanism by rotating along the central threaded rod, wherein a distal end (110) of the pusher is received in grooves (109) positioned on the clip such that pressure applied to the grooves is configured to push arms of the clip outward.

2. The spinal implant gripping device of claim 1, wherein the clip is configured with an audible mechanism that produces an audible sound when the gripping mechanism is fully engaged, indicating to the surgeon that the device is securely locked.

3. The spinal implant gripping device of claim 1, wherein the nut is reversible, allowing the device to transition between engaging and releasing the gripping mechanism.

4. The spinal implant gripping device of claim 1, wherein the clip includes contact surfaces made from non-damaging materials designed to protect fragile implant materials from wear or damage during the gripping process.

5. The spinal implant gripping device of claim 1, wherein the living hinges of the clip provide a progressive clamping force, gradually increasing until the clip is fully engaged, minimizing sudden or uneven pressure on the spinal implant.

6. The spinal implant gripping device of claim 1, wherein the central threaded rod includes an interface at its top for precise rotation and adjustment using standard surgical tools.

7. The spinal implant gripping device of claim 1, wherein the pusher exerts a controlled force on the living hinges of the clip to ensure even clamping pressure, reducing the risk of implant deformation or fracture.

8. The spinal implant gripping device of claim 1, wherein the device is configured to support itself in a locked position, allowing the surgeon to tap the implant into place using secondary tools without destabilizing the device or damaging the implant.

9. The spinal implant gripping device of claim 1, wherein the clip is designed to distribute clamping forces evenly across the spinal implant, ensuring secure engagement without compromising the structural integrity of the implant.

10. The spinal implant gripping device of claim 1, wherein the interchangeable nut can be used to adjust the position of the pusher for incremental adjustments of the gripping force applied by the pusher according to the degree of pressure applied to the grooves configured to push the arms of the clip outward.

11. The spinal implant gripping device of claim 1, wherein the device is constructed from materials selected for durability and compatibility with sterilization processes, ensuring repeated surgical use without degradation in performance.

12. The spinal implant gripping device of claim 1, wherein the pusher is configured to slide smoothly over the central threaded rod, reducing operational friction and enabling precise control during implant manipulation.

13. The spinal implant gripping device of claim 2, wherein the audible mechanism provides both tactile and auditory confirmation to the surgeon, enhancing operational
reliability during surgical procedures.

* * * * *